United States Patent [19]

Newman

[11] Patent Number: 4,704,088

[45] Date of Patent: * Nov. 3, 1987

[54] DENTAL MATERIALS DISPENSER AND APPLICATOR

[76] Inventor: Martin H. Newman, 77 Norwood St., Sharon, Mass. 02067

[*] Notice: The portion of the term of this patent subsequent to Apr. 15, 2003 has been disclaimed.

[21] Appl. No.: 815,373

[22] Filed: Dec. 31, 1985

Related U.S. Application Data

[63] Continuation of Ser. No. 604,923, Apr. 27, 1984, Pat. No. 4,582,488.

[51] Int. Cl.$^4$ .............................................. A66C 5/02
[52] U.S. Cl. ..................................................... 433/81
[58] Field of Search ...................... 433/80, 81, 89, 90; 222/326, 327

[56] References Cited

U.S. PATENT DOCUMENTS

| | | | |
|---|---|---|---|
| 3,900,954 | 8/1975 | Dragan | 32/60 |
| 4,171,072 | 10/1979 | Davis, Jr. | 222/326 |
| 4,198,756 | 4/1980 | Dragan | 222/326 |
| 4,265,618 | 5/1981 | Herskovitz et al. | 433/32 |
| 4,295,827 | 10/1981 | Martin et al. | 433/81 |
| 4,315,743 | 2/1982 | Brugirard | 433/90 |
| 4,330,278 | 5/1982 | Martin | 433/81 |
| 4,330,280 | 5/1982 | Dougherty et al. | 433/90 |

OTHER PUBLICATIONS

J. of Endodontics, vol. 7, No. 6, Jun. 1981, pp. 271-281.
Unitek Obrura—Heated Gutta-Percha Delivery System—11 pages, (Aug. 1978).

*Primary Examiner*—Robert Peshock
*Attorney, Agent, or Firm*—George W. Neuner; Robert F. O'Connell; Ronald I. Eisenstein

[57] ABSTRACT

A dental materials dispenser is disclosed with an actuator operated by an electronically controlled motor. The dispenser may be used in conjunction with a disposable cartridge removably mountable in the dispenser. The cartridge includes a hollow needle comprising an integral heating element along its length. An electronic controller regulates the speed and direction of the motor and the current delivered to the heating element.

6 Claims, 18 Drawing Figures

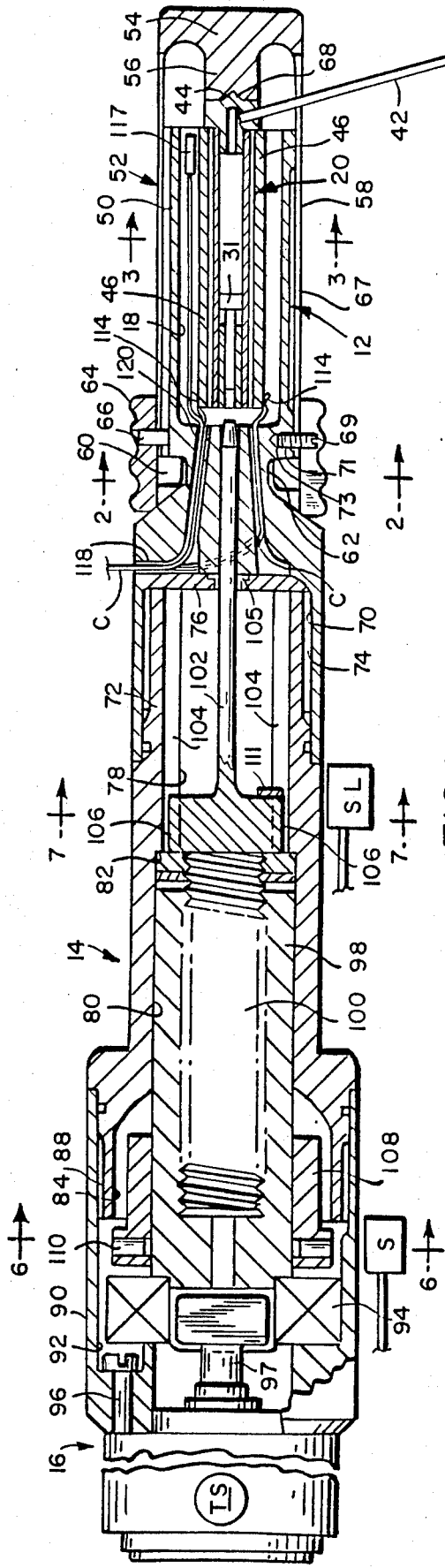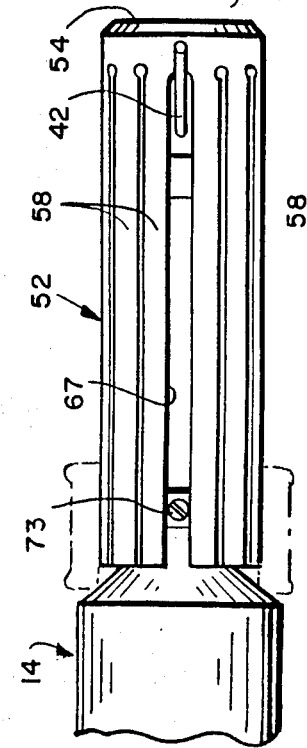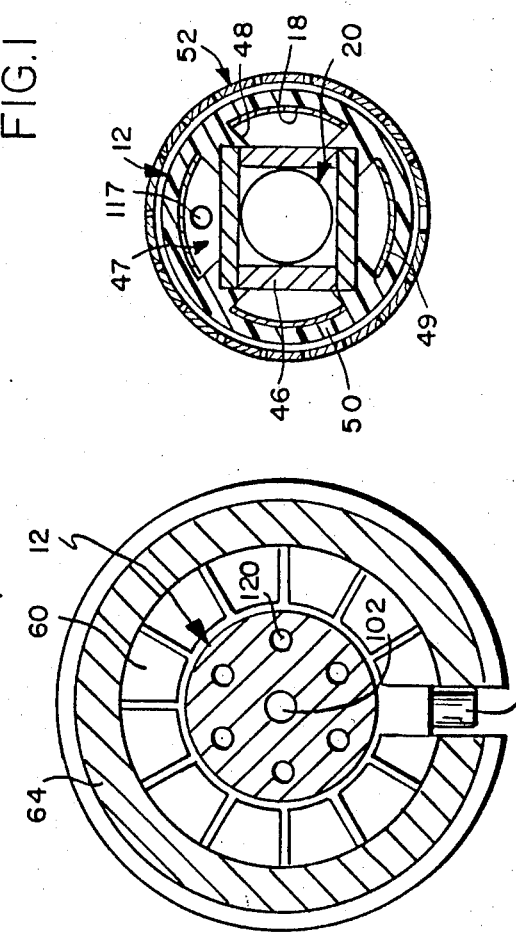

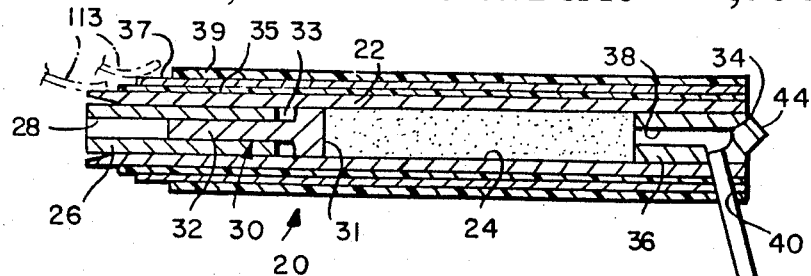
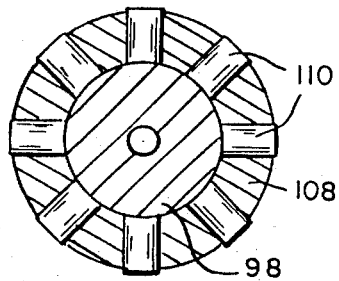
FIG.5
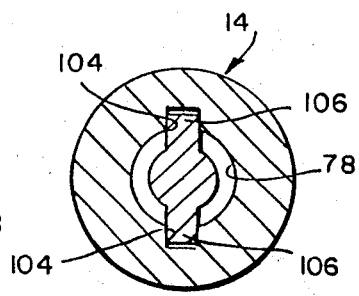
FIG.6   FIG.7
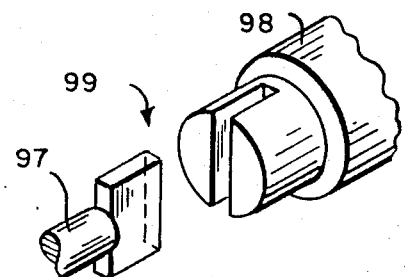
FIG.8
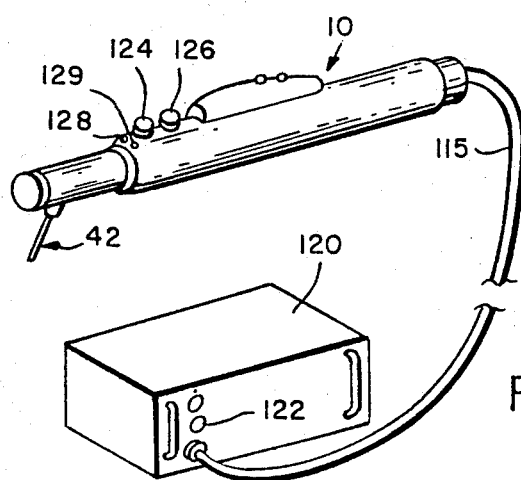
FIG.10
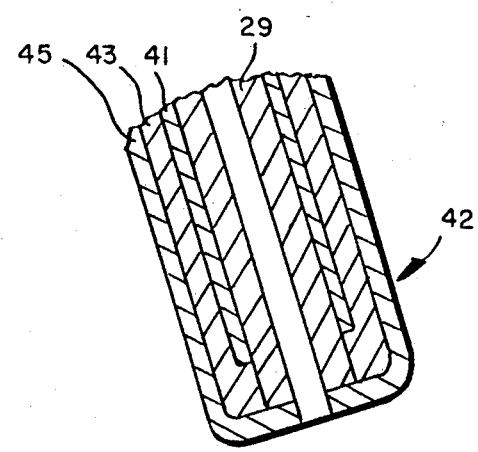
FIG.9

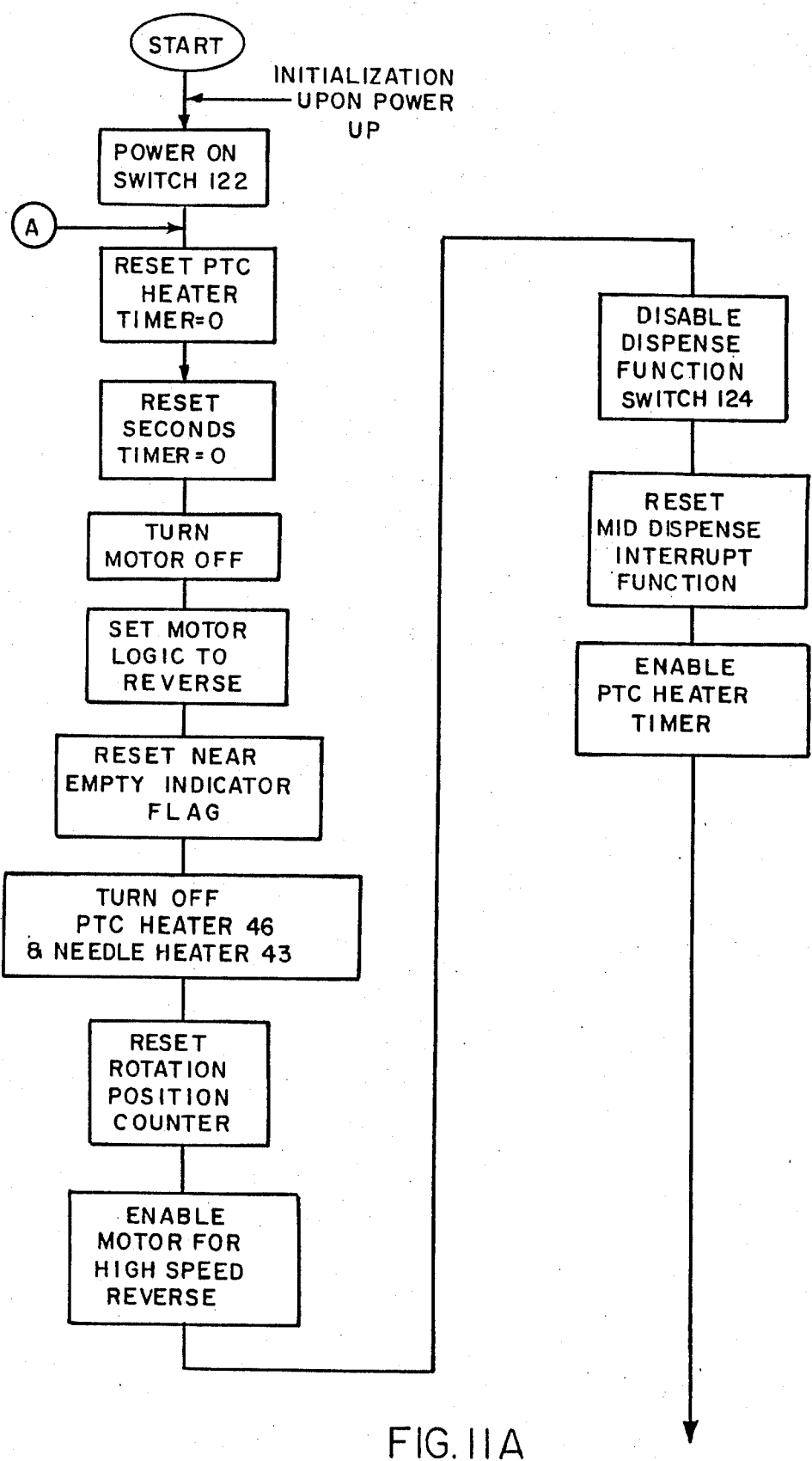
FIG. IIA

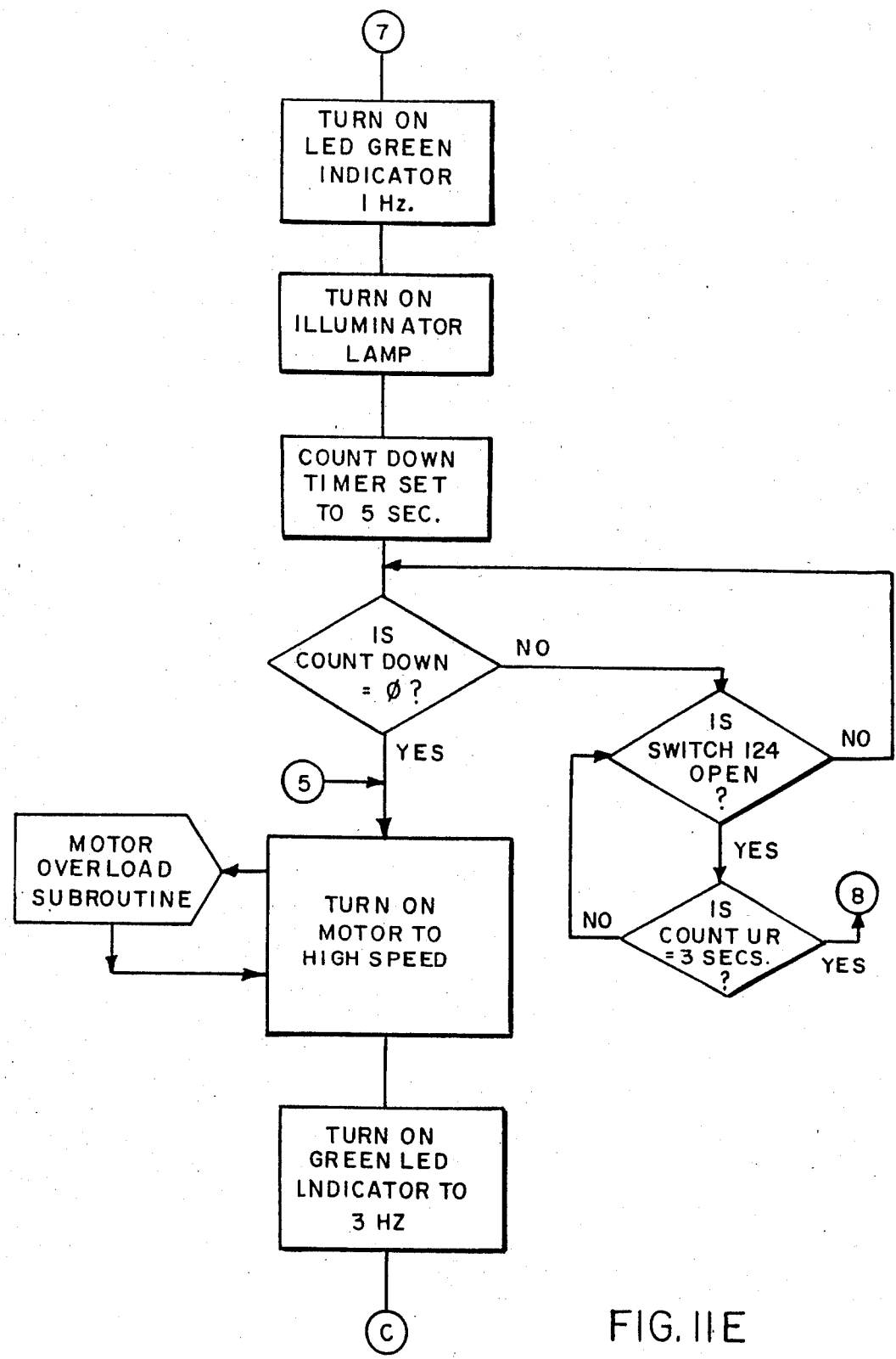
FIG. IIE

DENTAL MATERIALS DISPENSER AND APPLICATOR

This is a continuation of co-pending application Ser. No. 604,923 filed on 4/27/84, now U.S. Pat. No. 4,582,488.

BACKGROUND OF THE INVENTION

This invention relates to an apparatus for dispensing and applying dental materials. In particular, the invention is directed to a device for effecting ejection of an extrudable dental material such as gutta percha into a root canal, and to cartridges for holding and heating dental materials in connection with said device.

Endodonic dispensers such as are known and disclosed in the art are manually actuated. These manually operated devices require one hand to squeeze a lever or press a plunger while the other hand is used to manipulate the device for positioning the probe. With these cumbersome devices, it is very difficult to accurately and precisely position the probe. It is accordingly a purpose of the present invention to provide a power driven dispenser so that manual operation is not required. Hence, both hands can be used to guide and to direct the applicator into the best possible position for accomplishing the intended purpose and with the least danger or discomfort to the patient. It is a further purpose of the present invention to provide a device which is relatively simple to manufacture and maintain. It is also a purpose of this invention to provide a disposable cartridge for dental materials to be used with the automatic dispensing device of this invention.

U.S. Pat. No. 3,900,954 to Dragan discloses a dental filling gun with a manually operated plunger. The dental filling gun includes a detachable plastic nozzle tip which defines a reservoir for containing a predetermined amount of dental filling material. U.S. Pat. No. 4,265,618 to Herskovitz et al. discloses an endodontic syringe that contains an electrical heating section in the syringe barrel. Heated thermoplastic material is ejected through a hollow needle. The needle is made from a material having a high coefficient of thermal conductivity and the heat from the electrical resistance heater in the syringe barrel is conducted thermally into the needle to maintain the needle above 230° F. The heat enables the thermoplastic material to flow through the needle. A manual plunger is provided in the syringe barrel for ejecting the flowable material.

Suitable materials having a high coefficient of thermal conductivity for use in the heater body, hub and needle are very costly. Herskovitz et al. suggests the use of silver or copper. It is an object of the present invention to provide an electrically heated device for dispensing endodontic materials without resorting to extensive use of these high cost materials. Thus, advantageously, the present invention provides disposable cartridges which comprise integral heating elements for maintaining the extruded material in a flowable condition until it exits from the end of a thin elongated hollow probe.

SUMMARY OF THE INVENTION

As herein illustrated, the dental materials dispenser comprises an elongate holder having an elongate passage within an axial chamber. There is a hollow needle at one end of the passage and a piston at the other end. An actuator supported within the axial chamber of the elongated holder is in axial alignment with the piston. Means are provided for moving the actuator to cause the piston to push material through the needle. The preferred means for moving the actuator is an ACME screw assembly coupled through a driving element to a variable speed reversible motor. A switch is provided for operating an electronic controller which controls the speed and direction of the motor. Thus, the cumbersome manually operated plungers and levers have been replaced by an electronically controlled motor.

According to a further aspect of the invention, an electrical heating element extends along the length of the hollow needle. An electrical heater is also provided about the elongated passage containing the extrudable material. The inclusion of an electrical heating element as an integral part of the needle has severely reduced the need for expensive thermally conductive materials in the needle and surrounding the material in the elongated passage. This has made possible the use of disposable cartridges which carry the extrudable material and comprise an integral electrical heating element in the needle.

The disposable cartridge assembly of the present invention includes a cartridge cylinder which defines an elongated passage. A piston is positioned at one end of the passage and a distributor plug is positioned at the other end. A charge of flowable material is stored within the passage of the cartridge. A hollow needle is connected at one end to an opening in the distributor plug so that its interior is in communication with the interior of the passage of the cylinder. An electrical heating element is provided as an integral part of the cartridge to heat the flowable material. The piston is movable in the passage to effect discharge of the material from the passage and through the needle or probe.

The dispensing device for operating in conjunction with a disposable cartridge comprises an elongate holder for receiving the cartridge. Means are provided for removably mounting the cartridge in the axial chamber of the holder so that electrical conductor means within the elongate holder makes electrical connection with the heating element of the cartridge. The mounting means is preferably a sleeve-like collet telescoped over the structure on which it is positioned. There is a means for removably fixing the collet to the structure. Desirably, the disposable cartridge and its probe are jacketed with an insulating material.

Other objects and advantages of the invention will become apparent during the following description of the presently preferred embodiment of the invention taken in conjunction with the drawings.

BRIEF DESCRIPTION OF THE DRAWINGS

FIG. 1 is a foreshortened elevation partly in cross section of the materials dispenser of the invention;

FIG. 2 is a diametral section taken along the line 2—2 of FIG. 1;

FIG. 3 is a diametral section taken along the line 3—3 of FIG. 1;

FIG. 4 is a fragmentary elevation of the cartridge receiving portion of the dispenser;

FIG. 5 is a cross section of the cartridge assembly;

FIG. 6 is a diametral section taken along the line 6—6 of FIG. 1;

FIG. 7 is a diametral section taken along the line 7—7 of FIG. 1;

FIG. 8 is a fragmentary perspective of the coupling between the driving member of the ACME NUT assembly and the driven shaft connected to the motor;

FIG. 9 is an enlarged cross section of the distal end of the needle;

FIG. 10 is a perspective view of the dental material dispenser of the present invention.

FIGS. 11a–h are flow charts of the operation of the electronic controller of the dispenser of the present invention.

DETAILED DESCRIPTION OF THE PREFERRED EMBODIMENT

Figure 11B:
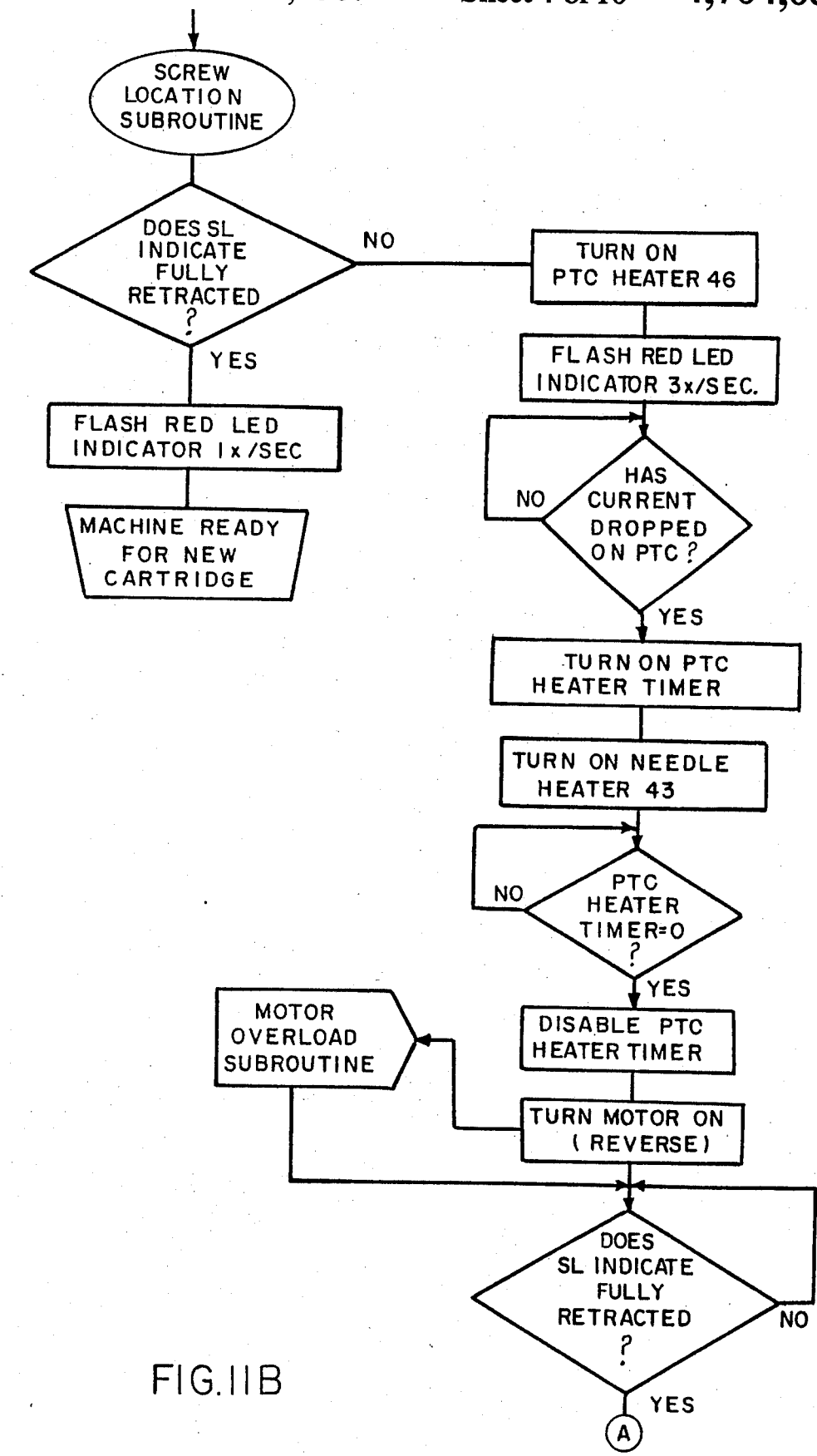

Referring to the drawings, the materials dispenser as shown in FIG. 1 of the drawings comprises a cartridge housing 12, a screw housing 14 and a motor housing 16, all of them elongate, cylindrical in cross section and joined end-to-end in alignment.

The cartridge housing 12 contains a cylindrical open end axial chamber 18 within which there is positioned a cartridge assembly 20, FIG. 5, comprising a cartridge cylinder 22 defining an elongate cylindrical passage 24 in one end of which is positioned a cartridge sleeve 26 defining a longitudinal bore 28. A piston 30 provided with a head 31 and a stem 32 is inserted into the bore 28 with a sealing washer 33 positioned between the head 31 and the end of the sleeve 26. At the opposite end of the cartridge cylinder 22, there is a distributor plug or head 34 provided with a neck 36 dimensioned to fit into the passage 24 so as to define with the piston head 31 a space for receiving a predetermined volume of the material to be dispensed. The preferred material for filling root canals with the present invention is gutta percha. The plug 34 contains an axial passage 38 and a lateral passage 40. A slender, hollow needle 42 is fixed at one end in the passage 40 and extends forwardly at an obtuse angle to the axis of the cylinder 22 and radially away from the plug. At the outer end of the plug 34, there is a conical centering nub 44.

Electrically conductive and insulating layers are applied to both the exterior surface of the cartridge cylinder and to the exterior surface of the needle. Specifically, in FIG. 5, there is an inner insulation layer 35 substantially coextensive in length with the cartridge cylinder 22 applied to the external surface of the cartridge cylinder 22. The insulation layer 35 comprises a dielectric material such as Parylene or polyamide approximately 0.1 mil thick. An electrically-conductive coating 37 is applied to the external surface of the insulation layer 35. The conductive coating 37 has a resistance of approximately one-half ohm along the length of the cartridge cylinder. A second insulation layer 39 of a dielectric as in layer 35 is applied to the outer surface of the electrically conductive coating 37. Connected with these layers, are corresponding insulating and electrically-conductive layers on the needle as shown in FIG. 9. The insulation preferably is a dielectric material such as Parylene, Teflon, Pyrol ML or some other equivalent material. The inner insulation layer 41 (FIG. 9) is preferably made of 1 mil. thick Teflon. The insulation layer 41 separates an electrically-resistive coating 43 from a stainless steel tube 29 which forms the inner canal through the needle and acts as the return path for electric current which flows to the tip of the needle 42 through the electrically conductive coating 37 on the cartridge and the resistive coating 43 in the needle. The electrically-resistive coating 43 has a resistance of 8 ohms along the length of the needle. The electrically resistive coating is preferably comprised of a mixture of silver and epoxy, which is available from Dupont. The thickness of coating 43 is appropriately adjusted to achieve approximately the 8 ohms of resistance necessary for proper functioning as a heating element. An outer insulation layer 45 of Teflon is provided to protect the patient from electrical shock. The minimum power rating for the electrically-resistive coating 43 is approximately 2.5 watts. The plug 34 is stainless steel and provides for electrically coupling the cylinder 22 in the cartridge body to the stainless steel cylinder 29 in the needle.

The cartridge assembly 20 is supported within the chamber 18 in concentric relation to its longitudinal axis within an insulating housing 47, FIG. 3, having quadrilaterally-positioned heating strips 46 positioned about the cartridge cylinder in tangential relation thereto and supported therein by spacer members 48 positioned about the interior of the cartridge holder 12, for engagement with the corners of the quadrilateral defined by the heating strips 46. The spacer members 48 are integral with a sleeve 50 defining the chamber 18. Desirably, the sleeve 50 and spacer members 48 are comprised of silicone rubber and the heating strips 46 are comprised of positive temperature coefficient ceramic, PTC. The inside surface of the sleeve 50 is coated with a heat reflective surface layer 49.

The cartridge assembly 20 is held in the chamber 18 by a collet 52, FIG. 4, defined by a solid head 54, at the center of which there is a boss 56 (FIG. 1) and peripherally-spaced, longitudinally-extending, flexible fingers 58, the distal ends of which terminate in radial locking lugs 60, FIG. 1. The collet is dimensioned interiorly to be slidably engaged with the exterior surface of the cartridge housing 12 and to be removably locked in engagement with the housing 12 by engagement of the locking lugs 60 with a recess 62 formed peripherally of the housing 12 which are held engaged thereby by an annular ring 64. The annular ring 64 has fixed within it a pin 66 which, by engagement with a longitudinal slot 67 in the collet, locates the sleeve in a position such that a diametrically-positioned hole 69 aligns with a threaded hole 71 in the housing for receiving a locking screw 73. The collet can be removed by removing the locking screw 73. Removal of the collet permits removal of the cartridge assembly. The boss 56 contains a recess 68 for receiving the nub 44 of the distributor head 34 so as to hold the cartridge assembly centered and locked in place.

The cartridge holder 12 defines, in addition to the chamber 18, an axially-spaced concentric chamber 70 within which one end 72 of the screw housing 14 is received and fixed desirably by cooperative threading 74 on the inner surface of the cartridge housing 12 and the outer surface of the screw housing 14. A resilient washer 76 is positioned within the chamber 70 and the threaded end of the screw housing is screwed into abutment with the resilient washer 76. The screw housing 14 defines a cylindrical chamber 78 of one diameter and a cylindrical chamber 80 of larger diameter arranged axially thereof which, in conjunction, defines an annular shoulder 82. At the end of the screw housing remote from the shoulder 82, there is a third chamber 84 in alignment with and concentric with the chamber 80. The enlarged end of the screw housing 14 is provided with threading 88 by means of which it is connected to cooperative threading of a coupling member 90 which defines a bearing chamber 92 within which is positioned a bearing assembly 94. The coupling 90 is bolted by means of bolts 96 to the motor housing 16 within which the motor is confined.

An ACME screw assembly comprising a drive member 98 and a driven member 100 is positioned in the chamber 80 with one end of the driving element restrained by the shoulder 82 and the other seated against the bearing assembly 94 for rotation about a longitudinal axis which is coaxial with the cartridge assembly. The driving member 98 is in the form of a motor and is internally threaded for receiving the driven member 100 which is in the form of a screw. An actuator rod 102 is fixed at one end to the screw. The other end of the actuator rod 102 extends through a suitable sleeve bearing 105 in the cartridge housing 12 into the chamber 18 in alignment with the rear end of the cartridge assembly. There are diametrically-spaced grooves 104—104 in the wall of housing 14 within the chamber 78 and diametrically-positioned guides 106—106 fixed to the screw at its junction of the actuator therewith slidably engaged with the grooves 104—104. As thus structured, rotation of the driving element 98 will extend the screw 100 axially therefrom toward the cartridge assembly and thus move the actuator 102 into engagement with the cartridge sleeve 26. The sleeve 26 is forced against the washer 33 and the piston 30 to effect extrusion of material through the needle 42. The washer 33 is squeezed between the sleeve 26 and piston head 31. Thus, the washer 33 expands to form an abridgement seal to prevent material from being extruded behind the piston 30. The guides 106—106 and grooves 104—104 prevent rotation of the screw and, hence, the actuator, thus restricting the actuator to linear movement.

In one embodiment of the invention, at the end of the drive member 98 located within the chamber 84, there is a peripherally-positioned sleeve 108 fixed to the drive member which has spaced peripherally thereof position sensing elements 110 in the form of magnets. The magnets are evenly spaced such that rotation of the drive member 98 an amount corresponding to the angular spacing between two adjacent magnets will be sensed by Hall effect device S and the amount of movement in the axial direction determined. Thus, the amount of remaining material in the passage 24 can be ascertained. The rotation of the elements 110 is sensed by the Hall effect device S which generates a signal representing a given angular rotation of the drive member 98. The drive member 98 can be driven by a DC reversible, variable speed motor, not shown, in the motor housing 16. An alternative preferred device for determining the angular rotation of the drive member 98 is an optical encoder disc which can be connected to the armature of the motor. Reduction gear, not shown, provides for coupling the drive shaft of the motor to a coupling member 97 which, in turn, is connected to the drive member 98 by a bayonet-type coupling 99, FIG. 8.

There is an indexing element 111 in the form of a magnet fixed to one of the guides 106 for linear and reciprocating movement with the screw. A sensing device SL exteriorly of the housing generates a signal indicating a fully-retracted position of the screw. Upon receiving this signal the control recognizes that a new cartridge can be mounted into the housing 12.

Power is supplied to the cartridge assembly by means of suitable conductors C which enter the cartridge housing 12 through radial and axial passages 118 and 120. There are wires 114 connecting a pair of conductors to the PTC heater 46. Another pair of conductors are connected to spring clips 113 slidably engageable with the externally exposed ends of the conductive layer 37 and the stainless steel cylinder 22 as shown in FIG. 5 to provide power to the heating element 43. A third pair of conductors C are connected to a thermister 117 which senses the temperature of the cartridge body.

Turning now to FIG. 10, the material dispenser 10 of the present invention is shown connected to its control box 120 via a cable 115. Signals from sensors S and SL are transmitted to the control box 120 through the cable 115. The cable 115 also carries the conductors C from the control box 120 to the material dispenser 10. Lines are also connected between the control 120 and the motor within housing 16. The control box 120 provides a power source and a preprogrammed controller. The presently preferred controller is a Texas Instruments TMS 7000 microprocessor.

The preprogrammed controller directs the operation of the material dispenser. A flow chart of the operation of the major programs within the processor are provided in FIGS. 11a–11g. Operation of the dispenser begins with actuation of a power switch 122 provided on the control box 120. A function touch switch 124 operates the dispenser on which it is located. A second switch 126 on the dispenser 10 is provided for independently operating a light (not shown) provided on the exterior of the dispenser and directed towards the tip of the needle to illuminate the work area. Activation of the power switch 122 turns the power on. Proceeding through the flow chart in FIG. 11a, the processor resets a PTC heater timer and a seconds timer to zero. The seconds timer is used as a count up timer to measure the time during which there is a pause in the midst of a dispensing operation. The motor is off. The motor logic is set to reverse. A near empty indicator flag is reset. The power to the heaters is off. A rotation position counter which counts the signals from sensor S is reset. The motor is enabled for high speed reverse. The function switch 124 on the dispenser 10 is disabled so that the dispenser cannot be operated in the forward direction yet.

The presently preferred dispenser may be interrupted and reversed when the operator quickly depresses function switch 124 three times. This activates a subroutine which is called a manual screw retract subroutine, FIG. 11g, which retracts the screw so that the cartridge may be replaced. This mid dispense interrupt function is reset when power switch 122 is turned on.

At this point in the program, a screw location subroutine as shown in FIG. 11b is performed. The screw location subroutine checks on whether the screw is at its fully retracted position as indicated by sensor SL. If the screw is fully retracted, the dispenser indicates that it is ready for a new cartridge by flashing a red LED 128 on and off every second. Otherwise, a routine is performed to turn on the cartridge heater 46 to soften any material that may have hardened while the material dispenser 10 was not being operated. The red LED 128 is flashed on and off quickly three times a second during heating. The cartridge PTC heater 46 becomes infinitely resistive at a predetermined temperature, preferably at least 180° F. Therefore, when the current to the PTC heater 46 drops, the desired temperature has been reached. The temperature may also be checked by using thermister 117. Once the temperature has been reached for a first time the needle heater 43 is turned on and the PTC heater timer is turned on and runs for about five minutes. This timer is provided since the PTC heater may cool below the desired temperature after it has first been reached. The five minutes allow for thermal stability to be reached within the cartridge. Then the motor is turned on in reverse and remains on until the sensor SL indicates that the screw has been fully retracted. While the motor is operating, a motor overload subroutine, shown in FIG. 11h is repeatedly checked. If the motor encounters an obstacle while retracting the screw, the electrical current to the motor will rise in attempting to overcome the obstacle. The rise in electrical current will cause the overload subroutine to be performed. The overload subroutine reverses the motor and attempts to move again, if the motor is still unable to move the red and green LED'S will alternately flash to indicate that a repair service should be called. If the motor moves, it will perform the flow chart from block B in FIG. 11d which retracts the screw so that the cartridge may be removed and replaced.

Figure 11C:
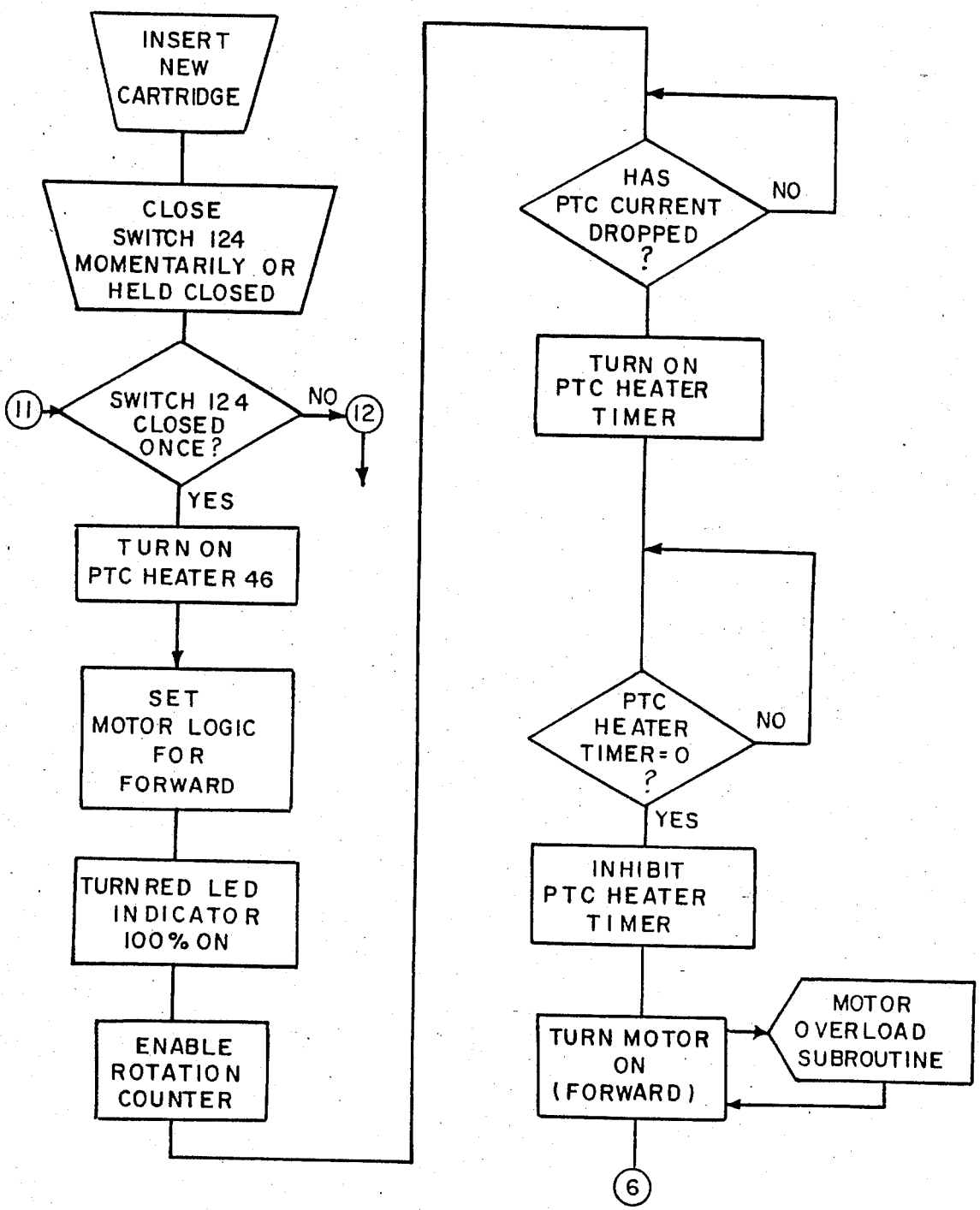

Referring now to FIG. 11c, the operation following the insertion of a new cartridge is shown. When the dispense switch 24 is depressed the material dispenser will begin initialization. However, if the switch 124 is depressed on and off three times within one and one-half seconds the manual screw retract subroutine is entered and the motor will retract the screw so that the cartridge may be removed. Returning to the initialization process, the PTC heater 46 is turned on. The motor logic is set for forward. The red LED is turned 100% on. The rotation counter which counts the pulses sent by sensor S indicating rotation of the screw drive number 98 is enabled. The current in the PTC heater is checked to see if the desired temperature has been reached. Once again, the thermister 117 may also be used to check the cartridge temperature. The PTC heater timer is set to about five minutes. The heater operates while the timer counts down to zero, allowing for thermal stability to be reached. During this time, the motor is off, preventing the actuator from moving until thermal stability is needed to completely soften the material in the cartridge. Then, the PTC heater timer is inhibited and the motor is turned on in a forward direction. If an obstacle is encountered while the motor is running, the motor overload subroutine is performed. In normal operation, the motor will remain on in a forward direction until ither the rotation counter indicates that the piston 30 has been pushed through more than 10% of the cartridqe or the motor current increases indicating that the piston 30 has encountered a load, presumably the gutta percha material. The motor current increases when actuator 102 encounters mechanical resistance in its forward motion against sleeve 26, said resistance being transmitted to the motor through the power train, comprising screw 100, nut 98 and coupling 97.

Figure 11D:
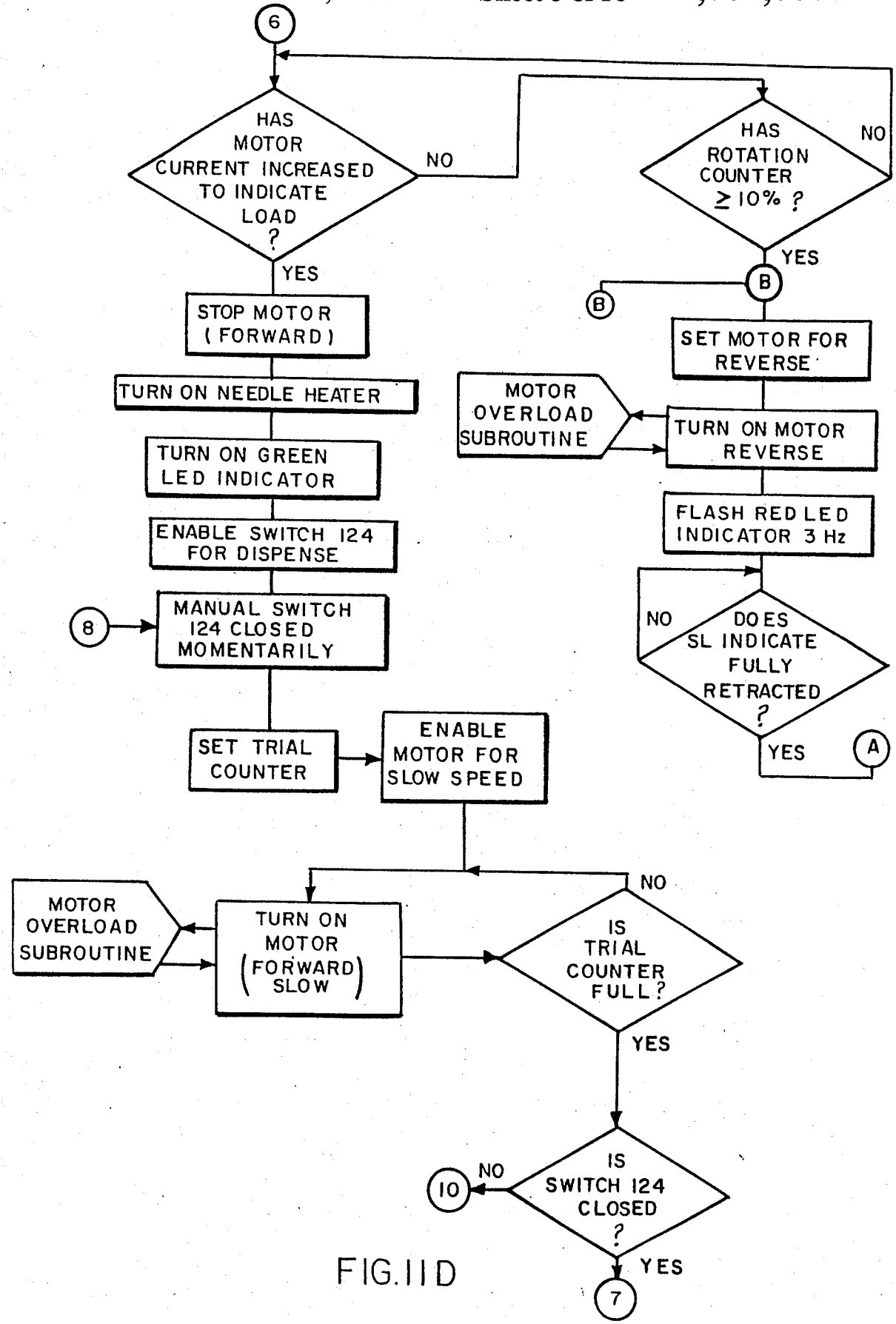

Referring now to FIG. 11d, when no material is found in the first 10% of the cartridge, the cartridge is considered defective. Therefore, an automatic reject is performed. This avoids commencement of operation with a partially empty cartridge so that the cartridge does not run out of material in the midst of filling a root canal. The motor is set into reverse and turned on in the reverse direction. The red LED flashes quickly at three times per second. The motor will continue to retract the screw until the sensor SL indicates that the screw has been returned to the zero location. The controller then returns to the start up routine so that the defective cartridge can be removed and replaced by a new cartridge.

If a load is indicated to be in the first 10% of the cartridge and has been encountered by the piston 30, the motor is stopped. The indication of a load generally means that the piston 30 has been moved into contact with material in the cartridge for the first time. It is then time for the needle heater 43 to be turned on so that material will be kept soft as it is extruded through the needle. The green LED indicator 129 is turned on. Switch 124 is enabled. When switch 124 is closed, a trial counter is set to permit approximately the number of rotations of the screw necessary to purge all of the air out of the needle 42. The trial counter is decremented in response to each rotation of the screw indicated by sensor S. The trial counter will start decremeting when the motor starts moving again after havinq encountered a load. From this point the trial counter counts down the number of rotations necessary to purge the air out of the needle and fill it completely with material. During the purge, the motor moves at a slow forward speed. The presently preferred slow speed is 0.143 inches/minute. At the completion of the purge, the dispenser is ready to begin dispensing material.

If switch 124 is closed, dispensing will begin. If the switch 124 is not closed, a patient counter which measures the time elapsing from the initial dispensing of material is set to thirty (30) minutes. The patient counter is provided to measure a predetermined time period that the dispenser can remain unused. Thirty minutes has been arbitrarily chosen as the maximum time period of inactivity. If this substantial time period elapses the dispenser will automatically retract the screw, refusing to further function with the used cartridge. This is a safety precaution provided so that each patient begins with a full fresh cartridge. After thirty minutes of non-use, it would be highly irregular for the same patient to be in the operating chair. Therefore, a fresh cartridge is required. (If a cartridge runs out of material in the middle of the filling of a root canal and a monlithic fill is desired, the material which has been put into the canal would have to be removed so that the material can be filled continuously until completed. This prevents any bacteria from growing in a void between successively applied layers.) The patient counter is provided to avoid use of a single cartridge to fill root canals in more than one patient. If the patient counter is not decremented to zero, switch 124 can be closed to dispense material.

Referring now to FIG. 11e for dispensing with switch 124 closed, the green LED 129 is flashed at a rate of one time per second indicating that switch 124 is depressed and the motor is driving the screw assembly at the slow speed. An illuminator lamp (not shown) is turned on. The lamp is directed towards the end of the needle 42. A countdown timer is set at approximately five seconds. This is the predetermined time period which has been provided for slow extrusion of the material. The extrusion of material must begin slowly so that the bottom of the root canal which may be opened to the soft tissue beneath the tooth can be capped to prevent bacteria or material irritants from entering the soft tissue beneath the tooth. During the slow mode of movement, if the function switch 124 is released a count up timer will be started. If three seconds elapse without the switch 124 being repressed, the countdown will stop and the controller will return to the point where it was waiting for depression of the switch 124 for dispensing material. When the switch 124 is pressed the dispenser will reinitiate the trial period and the 5 second slow period. If the switch 124 is repressed before 3 seconds elapses the motor will continue at slow speed until the 5 seconds have been counted down. After the five seconds of slow movement has been completed, the motor is switched automatically to high speed. The presently preferred high speed is 0.159 inches/minutes. The green LED, indicates this by flashing quickly three times per second, as long as switch 124 is depressed. If switch 124 is released, referring now to FIG. 11f, the count up timer starts counting seconds. If the pause in the actuation of switch 124 exceeds three seconds, the patient counter will bed set to the predeterminedd time period of 30 minutes. If the time period elapses without further use of the dispenser, the dispenser will enter the reject mode, retracting the screw and thereby preventing any further dispensing of material from the used cartridge. If the switch 124 is pressed before this, control will return to block 8 in the flow chart where the motor will begin at slow speed for the trial amount and then the five second period. If the pause does not exceed three seconds, repressing the switch 124 will cause the motor to return to high speed via block 5 in the chart.

Figure 11F:
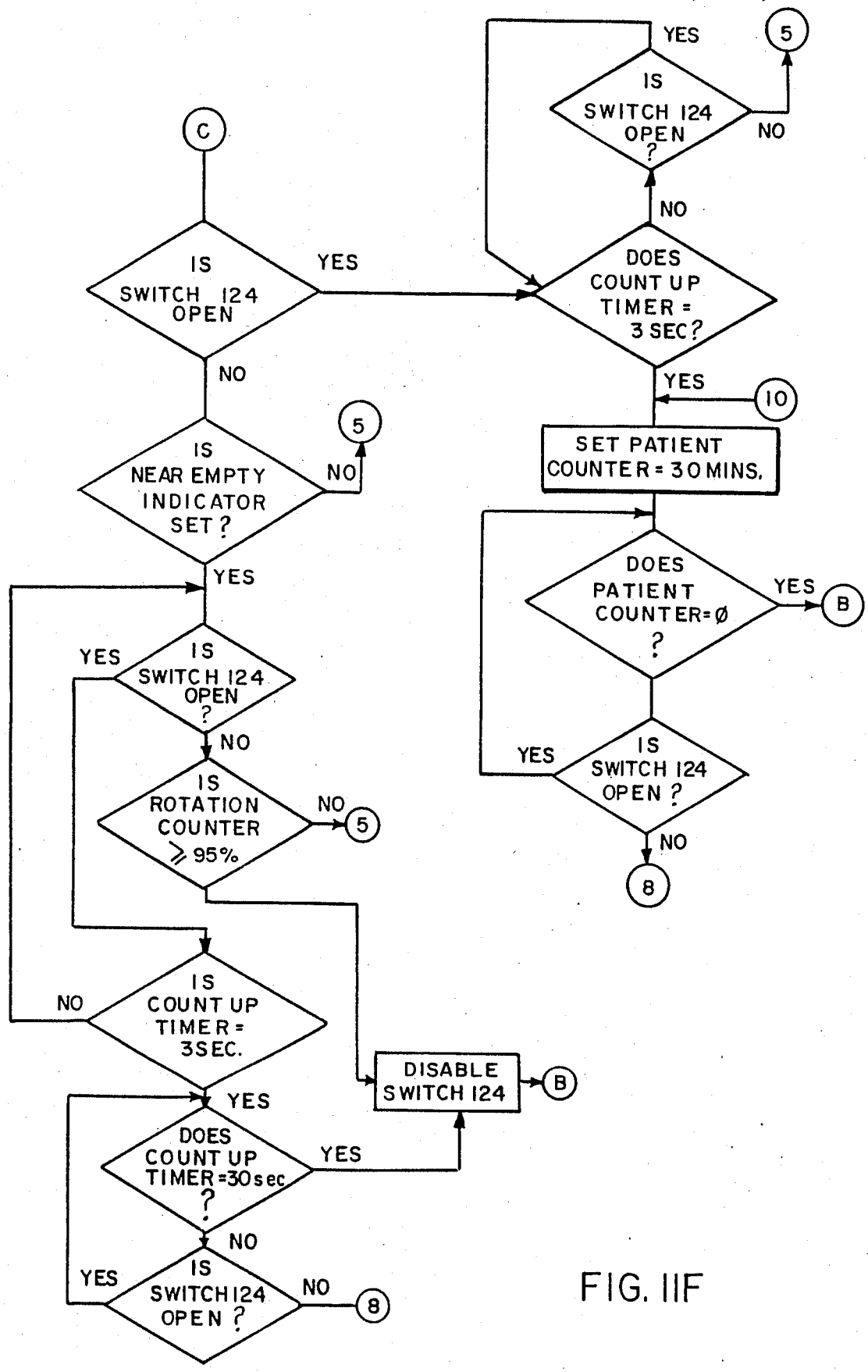

While the dispenser is operating at high speed a near empty indicator is checked as shown in FIG. 11f. If the cartridge is not near empty yet as determined by the count of position signals received from sensor S, the dispenser continues at high speed via block 5 in the chart. If the near empty indicator has been caused to be set, when the dispense switch 124 is opened, the count up timer is checked to see if the switch has been open for a substantial pause, which in the preferred embodiment is anything more than thirty seconds. If the pause is for less than three seconds, the dispenser is reactivated at high speed. If the pause is more than 3 seconds, but less than 30 seconds, the dispenser gets reactivated at slow speed. A delay of thirty seconds would indicate that the filling of a root canal in one tooth has been completed. the count up timer prevents any further operation of the dispenser after a thirty second delay to prevent an attempt at filling a second tooth with a cartridge that is near empty. Thus, when the cartridge is near empty and a delay in dispensing the material exceeds a substantial pause of thirty seconds, the dispense switch will be disabled and the motor will retract the screw so that the old cartridge can be removed.

As operation continues, the controller will check the rotation counter to see if it has reached an amount indicating that the cartridge is substantially empty of material. The presently preferred embodiment checks whether 95% of the cartridge has been dispensed. If this point has been reached, then the motor will reverse and the screw will be retracted so that the old cartridge can be removed. A full cartridge contains enough material to fill one full anterior canal or three small canals in a molar. Thus, in normal use the dispenser should not reach the 95% point. The controller continuously loops through its programs checking the timers and counters to ensure safe and proper operation of the dispenser.

Figure 11G:
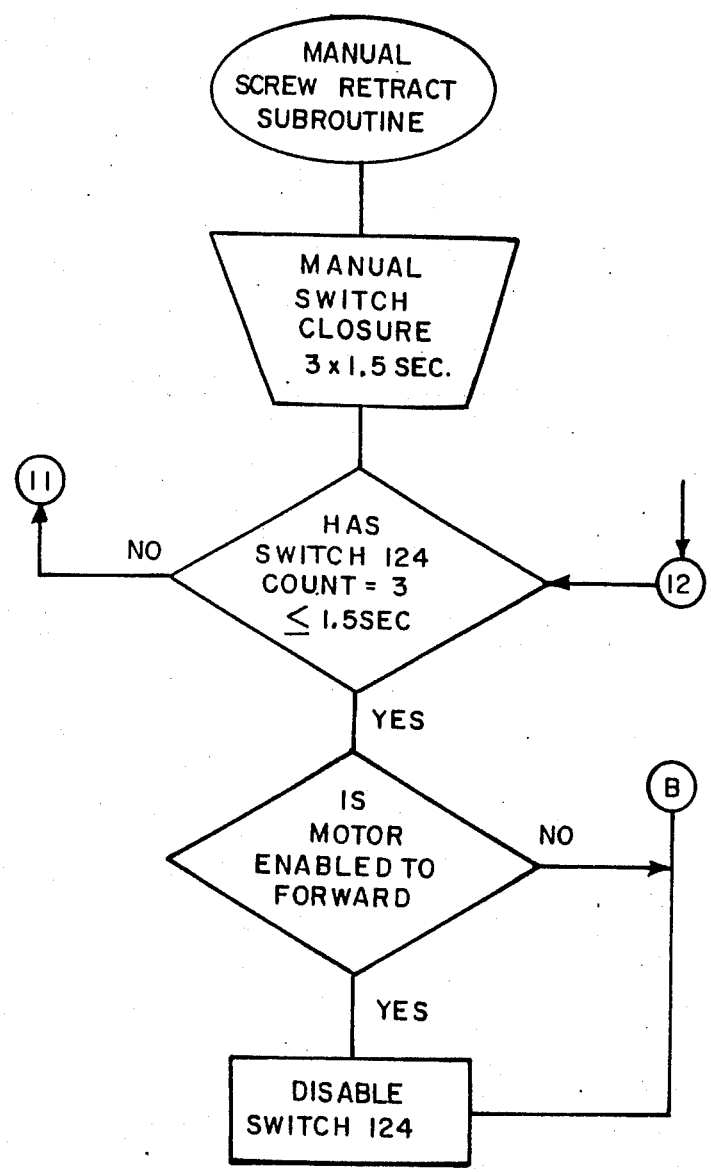
Figure 11H:
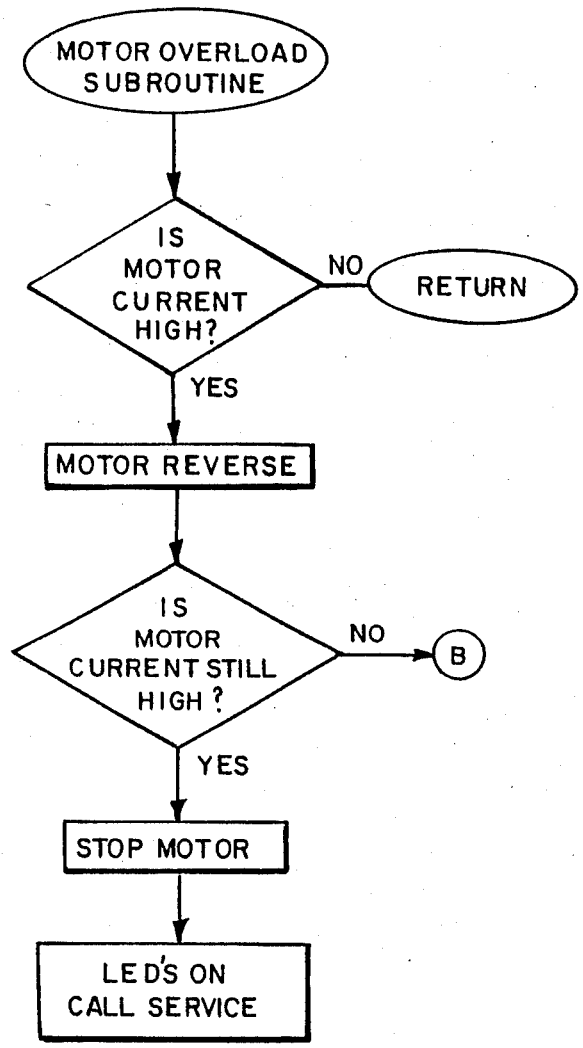

If at any time the operator is finished using the cartridge in the dispenser, the switch 124 can be pressed three times quickly, within 1.5 seconds, to cause the controller to perform the manual screw retract subroutine in FIG. 11g. The motor will be set to reverse and will fully retract the screw so that the old cartridge can be removed.

In using the dispenser for implanting a flowable material such as gutta percha into a root canal, it is only necessary to place a cartridge assembly containing a desired quantity of gutta percha in the dispensing implement, apply a voltage sufficient to fluidize the gutta percha and then to manipulate the dispenser in such fashion as to insert the distal end of the probe into the prepared and obturated root canal. Extrusion is effected at a controlled rate by the motor, thus relieving the technician of having to manually expel the implanting material and thus enabling the operator to pay close attention to the disposition of the probe for effectiveness and the least possible discomfort to the patient.

It should be understood that the present disclosure is for the purpose of illustration only and that one skilled in the art, upon considering the present disclosure may make modifications and improvements within the spirit and scope of the invention which includes all modifications or improvements which fall within the scope of the appended claims.

I claim:

1. A disposable cartridge assembly for a dental instrumentality designed to effect ejection of a flowable material for dental use, comprising:
   a cartridge cylinder defining an elongate passage of uniform cross section;
   a piston, having a stem and a head. positioned in the passage at one end of the cylinder;
   the other end of the cylinder containig a discharge opening;
   the passage between the piston and the other end providing a chamber within which is received a charge of flowable material;
   a hollow applicator needle fixed at the other end in the discharge opening such that the interior of said needle is in communication with the interior of the passage in the cylinder;
   said piston head being movable in the passage to effect discharge of material therefrom and through the needle.

2. The cartridge assembly of claim 1 wherein the hollow needle is a slender hollow needle fixed at one end in the discharge opening and extending forwardly at an obtuse angle to the cartidge cylinder and radially away from the distributor.

3. The cartridge assembly of claim 2 further comprising an electrical conductor means externally exposed at one end of the cylinder and connected to a heating element at the other end of the cylinder.

4. The cartridge assembly of claim 2 further comprising a sleeve positioned within the passage and surrounding the stem of the piston and a washer positioned between said sleeve and the head of the piston so that movement of the sleeve toward the piston head causes the piston head to move while the washer seals the passage.

5. A dental material dispenser comprising: an elongate holder containing a change of material and having a hollow needle at one end through which material can be extruded and a piston at the other end for expelling the material; an actuator supported in the chamber in axial alignment with the piston; means for moving the actuator axially to cause the piston to push material from the elongate passage through the needle; a driving element coupled to said means for moving the actuator; a motor coupled to said driving element for producing the movement of said actuator; manually controlled switch means for operating said dispenser; and electronic controller means, responsive to said switch means, for controlling the speed and direction of said motor, 6. A dental extruder for effecting ejection of an extrudable material into a root canal comprising an elongate holder containing an axial chamber for receiving a cartridge wherein the cartridge contains a charge of the extrudable material and compromises a hollow needle at one end through which the material can be extruded, and a piston at the other end for expelling the material; means, supported in the chamber, for moving the piston to cause material to be expelled from the cartridge through the needle.

* * * * *